US012637666B2

(12) United States Patent
Chen et al.

(10) Patent No.: US 12,637,666 B2
(45) Date of Patent: May 26, 2026

(54) PET HYDROLASE HAVING HIGH ENZYMATIC ACTIVITY

(71) Applicant: Hubei University, Wuhan City (CN)

(72) Inventors: Chun-Chi Chen, Wuhan City (CN); Jian-Wen Huang, Wuhan City (CN); Yu Yang, Wuhan City (CN); Jian Min, Wuhan City (CN); Yunyun Yang, Wuhan City (CN); Longhai Dai, Wuhan City (CN); Lilan Zhang, Wuhan City (CN); Yumei Hu, Wuhan City (CN); Hailin He, Wuhan City (CN); Xin Long, Wuhan City (CN); Du Niu, Wuhan City (CN); Rey-Ting Guo, Wuhan City (CN)

(73) Assignee: Hubei University, Wuhan City (CN)

( * ) Notice: Subject to any disclaimer, the term of this patent is extended or adjusted under 35 U.S.C. 154(b) by 355 days.

(21) Appl. No.: 18/338,606

(22) Filed: Jun. 21, 2023

(65) Prior Publication Data

US 2024/0263155 A1     Aug. 8, 2024

(30) Foreign Application Priority Data

Feb. 8, 2023   (CN) .......................... 202310115069.8

(51) Int. Cl.
*C12N 9/18*          (2006.01)
(52) U.S. Cl.
CPC ..................................... *C12N 9/18* (2013.01)
(58) Field of Classification Search
CPC ...................................................... C12N 9/18
See application file for complete search history.

(56) References Cited

FOREIGN PATENT DOCUMENTS

WO      WO-2022076380 A2 *   4/2022   ............... C12N 9/18

OTHER PUBLICATIONS

PETH_IDESA. UniProtKB/Swiss-Prot Database. Sep. 29, 2021 (Year: 2021).*
Fransceus (J Ind Microbiol Biotechnol. May 2017;44(4-5):687-695. (Year: 2017).*
Sanavia (Computational and Structural Biotechnology Journal, vol. 18, 2020, pp. 1968-1979. (Year: 2020).*
Studer. Residue mutations and their impact on protein structure and function: detecting beneficial and pathogenic changes. Biochem. J. (2013) 449, 581-594. (Year: 2013).*
WP_257828480.1 A. GenBank Database. Aug. 17, 2022 (Year: 2022).*
WP_257828480.1 B. GenBank Database. May 12, 2024 (Year: 2024).*
Sevilla. Degradation of PET Bottles by an Engineered Ideonella sakaiensis PETase. Polymers (Basel). Apr. 3, 2023;15(7): 1779 (Year: 2023).*

* cited by examiner

*Primary Examiner* — Yong D Pak
(74) *Attorney, Agent, or Firm* — KIRTON McCONKIE; Evan R. Witt

(57)          ABSTRACT

A PET hydrolase having high enzymatic activity is disclosed. The PET hydrolase has a modified amino acid sequence of SEQ ID NO: 2. The modified enzyme has improved PET-hydrolytic activity, thereby obtaining the high-yield and high-activity PET hydrolase, and enhancing the industrial application value of the PET hydrolase.

1 Claim, 7 Drawing Sheets
Specification includes a Sequence Listing.

| Mutant | Primer Sequence (5'→3') |
|---|---|
| N212A | CTCCAGTTGCTTCTTCCGCTTTGCCAATC (SEQ ID NO. 3) |
| N277A | CCCAGCTTCTACTGCTGTTTCTGACT (SEQ ID NO. 4) |

| Mutant | Primer Sequence (5'→3') |
|--------|-------------------------|
| N212A | CTCCAGTTGCTTCTTCCGCTTTGCCAATC<br>(SEQ ID NO. 3) |
| N277A | CCCAGCTTCTACTGCTGTTTCTGACT<br>(SEQ ID NO. 4) |

FIG. 2

PET HYDROLASE HAVING HIGH ENZYMATIC ACTIVITY

CROSS-REFERENCE TO RELATED APPLICATION

This application claims priority to China Patent Application No. 202310115069.8, filed on Feb. 8, 2023, the entire contents of which are incorporated herein by reference for all purposes.

INCORPORATION BY REFERENCE

The Sequence Listing XML having the file name "15258-1715_Sequence_Listing.xml", a creation date of Jun. 21, 2023, and a file size of 11 KB is incorporated herein by reference for all purposes.

FIELD OF THE INVENTION

The present invention relates to a PET hydrolase, and more particularly to a PET hydrolase having high enzymatic activity.

BACKGROUND OF THE INVENTION

Plastic products have been widely used in many aspects of life due to its high formability and stability and bring many conveniences to human life, but the resulted white pollution has seriously threatened the global ecosystem. At present, the global annual production of synthetic plastics has exceeded 400 million tons, wherein polyethylene terephthalate (PET) is a major contributor to the white pollution. PET is composed of ester bond-linked terephthalic acid (TPA) and ethylene glycol (EG), and is highly stable and difficult to decompose. PET is often used in mineral water bottles, polyester clothes and blister packs, which causes huge amount of waste. Since it takes hundreds of years to completely decompose synthetic plastic waste in natural degrading processes, the plastic waste has been continuously accumulated in the environment and invaded the human food chains. Accordingly, the plastic waste seriously threatens the earth's ecology and the human health, and has become one of the pollution problems of global concern.

The current treatments for PET waste mainly include landfill, incineration, recycling and biodegradation. Although landfill and incineration are the simplest, the generated waste gas and water will cause secondary pollution to the environment. As to recycling, due to the economic efficiency of recycling costs and the performance issues of recycled plastics, the recycling rate remains low at the moment. The biodegradation technology (enzymatic degradation or microbial degradation) can degrade PET into small molecules, which can be further recycled to synthesize PET. Therefore, the biodegradation technology solves the problem of PET waste, and can further recycle the raw materials for PET synthesis. Currently, the biodegradation technology has gradually become a research hotspot due to its environmentally friendly features. The scientists have been looking for effective PET biodegradation methods for a long time, and now they have found PET degradation activities from esterases, lipases and cutinases, proving the possibility of PET biodegradation. For example, TfH and TfH BTA-2 from *Thermobifida fusca*, LC cutinase from leaf compost, and lipase B from *Candida antarctica*, etc., have all been confirmed to have PET degradation activities. However, since PET is not the major reactant of the above-mentioned enzymes, the PET degradation rate is still low, resulting in low industrial application values of the above-mentioned enzymes.

In 2016, a Japanese research team reported magical bacteria named *Ideonella* sakaiensis that can "eat plastic". The bacteria can secrete a new type of PET hydrolase (IsPETase), which is able to decompose PET into small fragments of mono(2-hydroxyethyl) terephthalic acid (MHET) at 30° C., and the decomposed products can be further digested by the bacteria and finally converted into two simple molecules, terephthalic acid (TPA) and ethylene glycol (EG). IsPETase has relatively higher activity in degrading PET than other esterases or cutinases and thus has potential industrial application value. The scientists have also conducted a lot of subsequent researches to improve the activity of IsPETase. Recently, Hal S. Alper et al. at the University of Texas at Austin designed the engineering mutant PET hydrolases by machine learning algorithms based on IsPETase. They used *Pseudomonas putida* KT2440 to express the IsPETase wild-type protein and the designed mutants. The mutant with the highest activity was named FAST-PETase, which showed good PET-hydrolytic activity at 30~50° C. and neutral pH conditions. Although the PET-hydrolytic activity of the FAST-PETase has increased, the FAST-PETase has not been produced industrially so far, and there is still a long way from commercial application.

Therefore, the present invention intends to modify the FAST-PETase, so as to improve its PET-hydrolytic activity, thereby increasing its industrial application value.

SUMMARY OF THE INVENTION

An object of the present invention is to modify an existing PET hydrolase by means of structural analysis and site-directed mutagenesis for improving the PET-hydrolytic activity of the PET hydrolase and further increasing its industrial application value.

According to an aspect of the present invention, there is provided a PET hydrolase having high enzymatic activity. The PET hydrolase has the modified amino acid sequence of SEQ ID NO: 2, wherein the modification is a substitution of asparagine at position 212 with alanine, or substitutions of asparagines at both positions 212 and 277 with alanines.

In an embodiment, the PET hydrolase has the full length amino acid sequence of SEQ ID NO: 6.

In an embodiment, the PET hydrolase has the full length amino acid sequence of SEQ ID NO: 8.

According to another aspect of the present invention, there is provided a nucleic acid encoding the aforesaid PET hydrolase, and a recombinant plasmid comprising the aforesaid nucleic acid.

The above objects and advantages of the present invention will become more readily apparent to those ordinarily skilled in the art after reviewing the following detailed description and accompanying drawings, in which:

BRIEF DESCRIPTION OF THE DRAWINGS

FIG. 2 shows the primer sequences for site-directed mutagenesis;

DETAILED DESCRIPTION OF THE PREFERRED EMBODIMENT

The present invention will now be described more specifically with reference to the following embodiments. It is to be noted that the following descriptions of preferred embodiments of this invention are presented herein for purpose of illustration and description only; it is not intended to be exhaustive or to be limited to the precise form disclosed.

In view of the fact that the FAST-PETase has not yet been produced industrially, the present invention tries to study and further modify the FAST-PETase in order to increase its industrial application value. Firstly, it is found that the FAST-PETase can be effectively expressed in *Pichia pastoris*, which is commonly used in industry, and thus has potential industrial application value. The *P. pastoris* expression system has the advantages of low cost, high-density fermentation, high expression of exogenous proteins, external secretion, and capable of post-translational modification, such as glycosylation, phosphorylation and disulfide bonds formation, of exogenous proteins. The *P. pastoris* expression system has many advantages, however, other studies have also found that although the glycosylation modification can increase the thermal stability of the protein, if the glycosylation site is too close to the active region of the protein, the activity of the protein will also be affected. Therefore, in order to modify the FAST-PETase into a high-yield and high-activity PET hydrolase, the present invention further analyzed the tertiary structure of the protein, and selected glycosylation sites that may affect the activity for further modification. Particularly, the present invention utilized site-directed mutagenesis to mutate asparagine (N) at position 212 of the FAST-PETase into alanine (A), and simultaneously mutate asparagines (N) at both positions 212 and 277 of the FAST-PETase into alanines (A). The present invention successfully improved the PET-hydrolytic activity of the FAST-PETase, and further increased the industrial application value of the PET hydrolase. Hereinafter, the enzyme modification method and the resulted PET hydrolase having high enzymatic activity will be described in detail.

First, the FAST-PETase gene was obtained by gene synthesis, and the gene was constructed into pPICZαA vector using EcoRI and NotI restriction enzymes. Then the recombinant plasmid was transformed into a competent cell to obtain the FAST-PETase recombinant plasmid.

Figure 1:
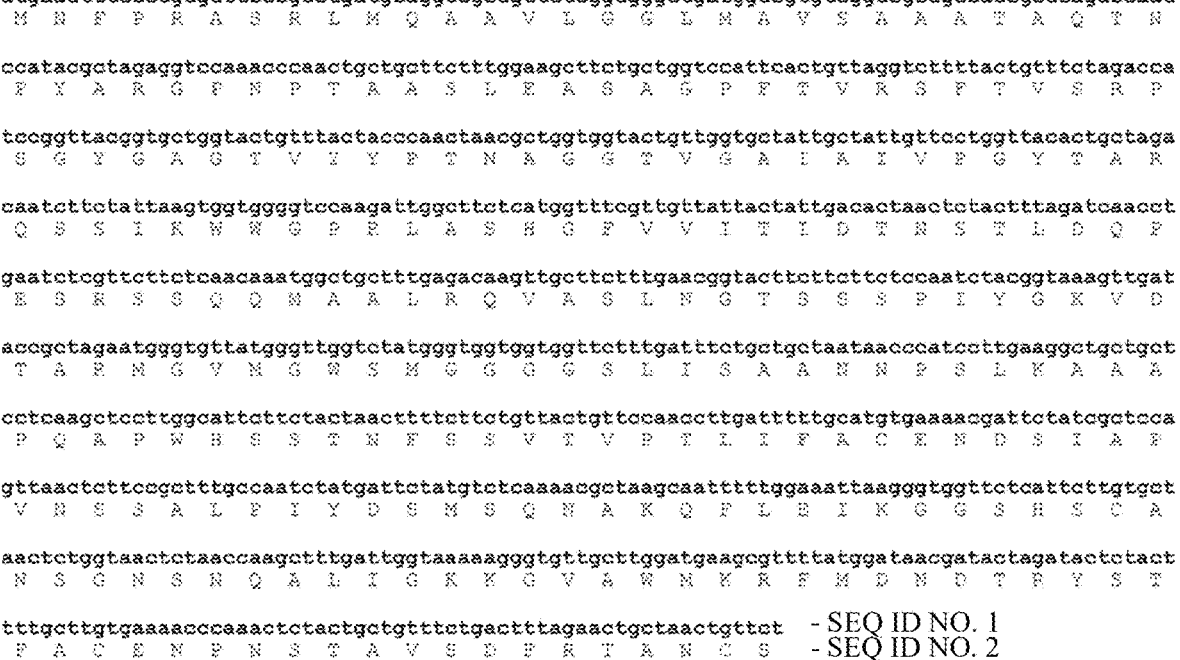
FIG. 1 shows the nucleotide sequence and the amino acid sequence of the FAST-PETase.

FIG. 1 shows the nucleotide sequence and the amino acid sequence of the FAST-PETase, wherein the FAST-PETase gene consists of 870 base pairs (SEQ ID NO: 1) and encodes 290 amino acids (SEQ ID NO: 2).

Figure 3:
FIG. 3 shows the nucleotide sequence and the amino acid sequence of the mutant FAST-PETase-N212A.
Figure 4:
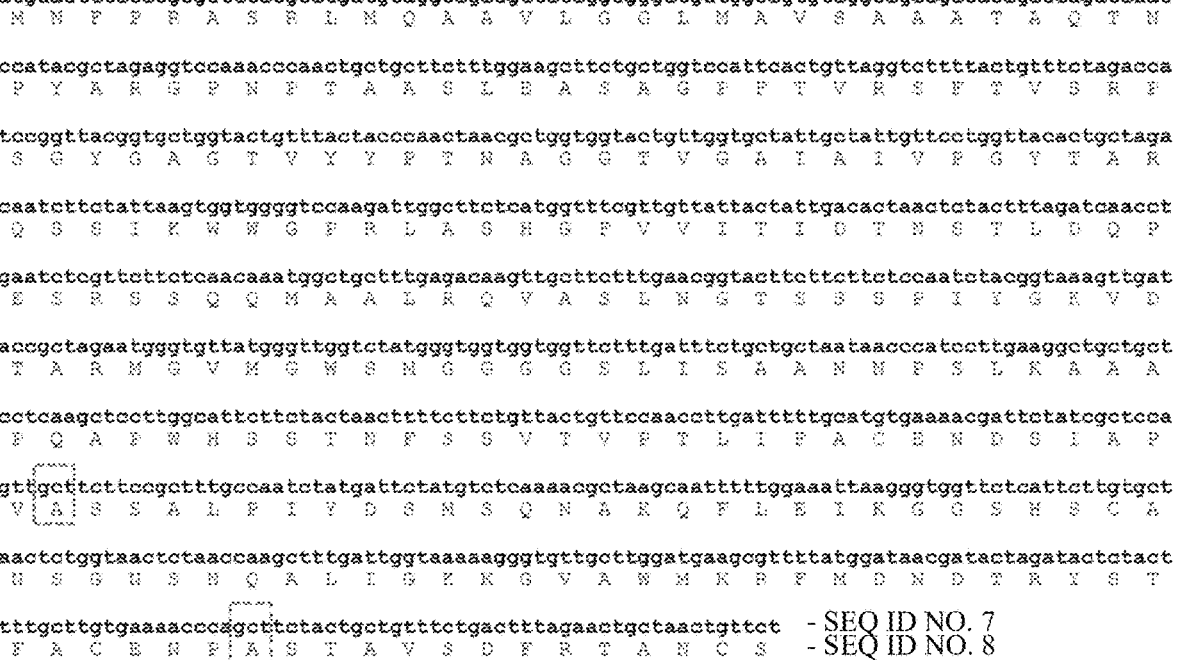
FIG. 4 shows the nucleotide sequence and the amino acid sequence of the mutant FAST-PETase-N212A/N277A.

In order to improve the PET-hydrolytic activity of the FAST-PETase, the present invention utilized site-directed mutagenesis by using the wild-type FAST-PETase gene as the template and using the mutant primers shown in FIG. 2 to perform the polymerase chain reaction (PCR). The mutant primers include the mutant primer N212A (SEQ ID NO. 3) to mutate asparagine (N) at position 212 into alanine (A) and the mutant primer N277A (SEQ ID NO. 4) to mutate asparagine (N) at position 277 into alanine (A). The original template DNA was then removed using DpnI. Subsequently, the mutant plasmid was transformed into *E. coli* competent cells, and the mutant gene was confirmed by DNA sequencing. Here, the present invention constructed two mutant strains of the FAST-PETase, which are FAST-PETase-N212A and FAST-PETase-N212A/N277A. The FAST-PETase-N212A means that asparagine (N) at position 212 of FAST-PETase is substituted with alanine (A). The FAST-PETase-N212A/N277A means that asparagines (N) at both positions 212 and 277 of FAST-PETase are substituted with alanines (A). FIG. 3 shows the nucleotide sequence and the amino acid sequence of the mutant FAST-PETase-N212A, wherein the FAST-PETase-N212A gene consists of 870 base pairs (SEQ ID NO. 5) and encodes 290 amino acids (SEQ ID NO. 6). FIG. 4 shows the nucleotide sequence and the amino acid sequence of the mutant FAST-PETase-N212A/N277A, wherein the FAST-PETase-N212A/N277A gene consists of 870 base pairs (SEQ ID NO. 7) and encodes 290 amino acids (SEQ ID NO. 8).

The following is to further express and purify the proteins in *P. pastoris*. First, the constructed recombinant plasmids FAST-PETase-N212A and FAST-PETase-N212A/N277A were linearized by PmeI and then transformed into *P. pastoris* by electroporation, respectively. The transformants were selected on YPD plates containing 250 μg/ml zeocin and incubated at 30° C. for 2 days. The selected colonies were inoculated in 5 ml YPD medium at 30° C. for 18 hours, and then amplified in 500 ml BMGY medium at 30° C. to the next day. Then, a total of 0.5% methanol was supplemented every day to induce protein expression. After 4 days of protein induction and expression, the medium was centrifuged at 3500 rpm and the supernatant was collected for the next step of purification. To obtain high-purity enzyme protein, the present invention used nickel ion chromatography column and SP cation exchange column sequentially to purify protein by fast protein liquid chromatography (FPLC). Finally, the purified target protein was concentrated in the buffer containing 20 mM Tris-HCl, 150 mM NaCl, pH 7.5 and stored at −80° C.

The PET-hydrolytic activities of the three PET hydrolases were measured to compare the activity difference between the FAST-PETase and the mutants. The method for measuring the PET-hydrolytic activity was as follows. The reaction buffer contained 50 mM glycine, pH 9.0, and each reaction mixture (1 mL) included amorphous PET film (GfPET purchased from Goodfellow with crystallinity of 7.3%) and 10 μL of enzyme (1 mg/mL). After mixing, the reaction tube was incubated in a metal bath of 50° C. with agitation at 800 rpm for 6 hours. Each reaction condition was performed in triplet. The reaction was terminated by heating at 100° C. for 10 min. Then the reaction mixture was centrifuged at 12000 rpm for 10 minutes, and the supernatant was filtered through a 0.22 μm filter membrane. The filtered supernatant in each group was determined and analyzed by HPLC equipped with C18 column (4.6×250 mm, 5 μm). The mobile phase was methanol/phosphate (20 mM, pH 2.5), the flow rate was 1 ml/min, the detection wavelength is 254 nm, the elution condition is 0-15 minutes, and the methanol linear gradient is 35-70%.

Figure 5:
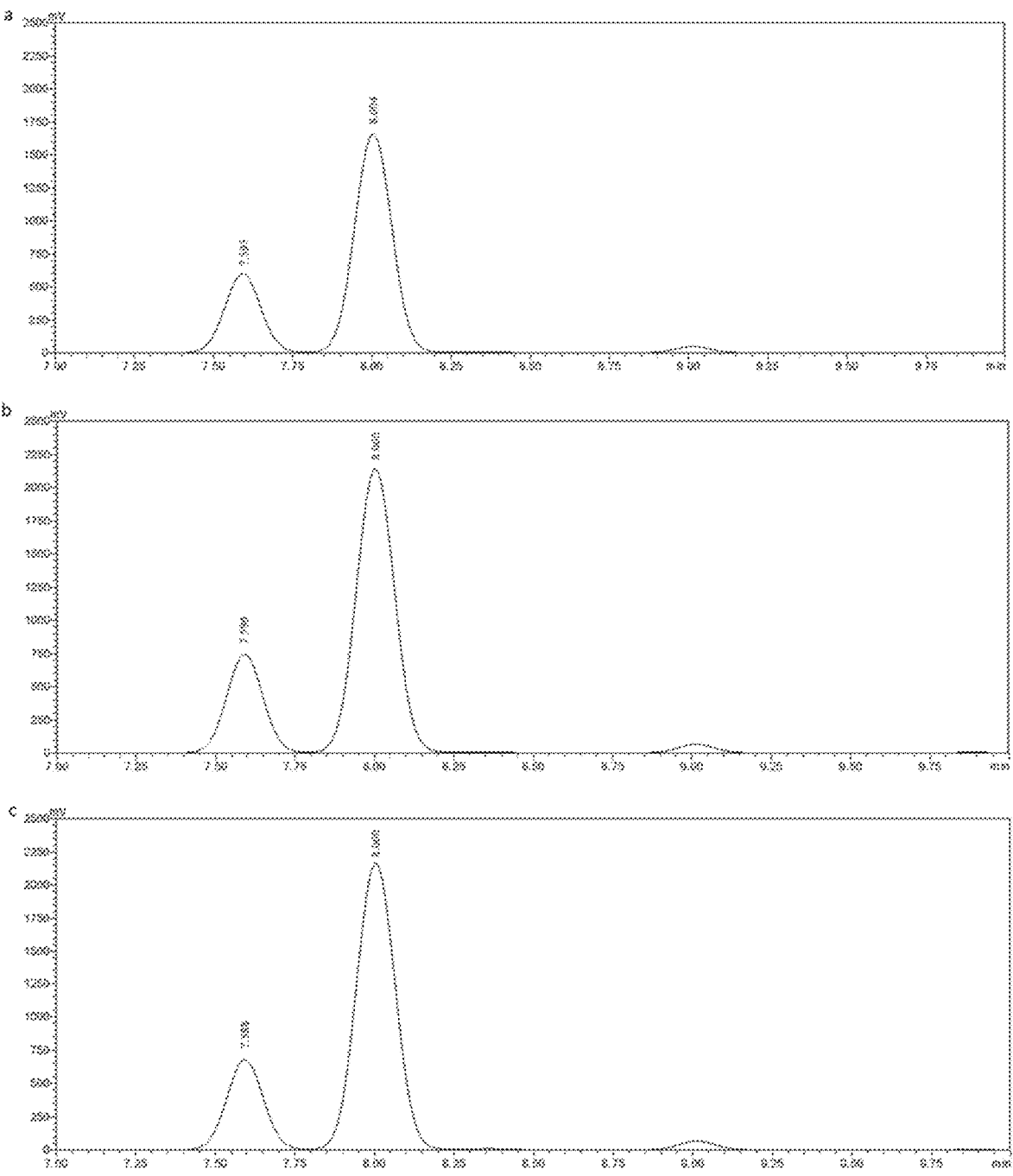
FIG. 5 shows the HPLC analysis of the PET degradation products resulted by the FAST-PETase and the mutants.
Figure 6:
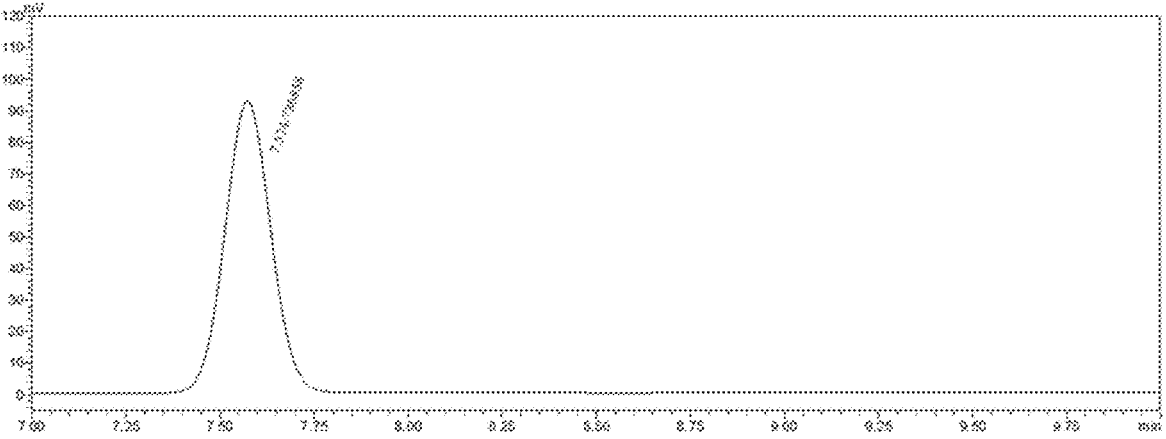
FIG. 6 shows the HPLC analysis of the standard product TPA.
Figure 7:
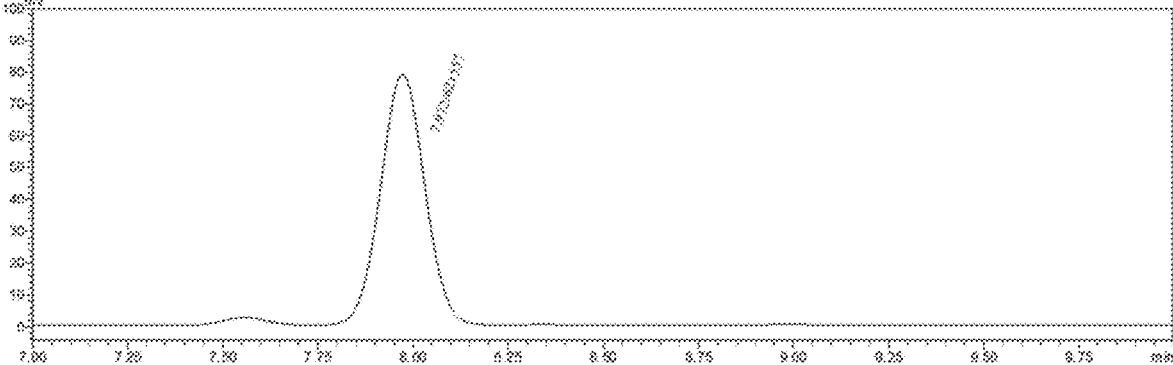
FIG. 7 shows the HPLC analysis of the standard product MHET.

FIG. 5 shows the HPLC analysis of the PET degradation products resulted by the FAST-PETase and the mutants, wherein the subfigure a shows the HPLC analysis for the FAST-PETase, the subfigure b shows the HPLC analysis for the FAST-PETase-N212A, and the subfigure c shows the HPLC analysis for the FAST-PETase-N212A/N277A. As shown in FIG. 5, all detections peaked at a retention time of 7.59 minutes and a retention time of 8.00 minutes. The peak time with a retention time of 7.59 minutes was consistent with the standard product TPA (FIG. 6), so the substance with a retention time of 7.59 minutes was TPA. The peak time with a retention time of 8.00 minutes was consistent with the standard product MHET (FIG. 7), so the substance with a retention time of 8.00 minutes was MHET. Then, the peak areas of the degradation products MHET and TPA of the FAST-PETase, the FAST-PETase-N212A and the FAST-PETase-N212A/N277A were respectively converted into product concentrations via the standard curves of MHET and TPA. The PET-hydrolytic activity was defined as the sum of the concentrations of MHET and TPA.

Figure 8:
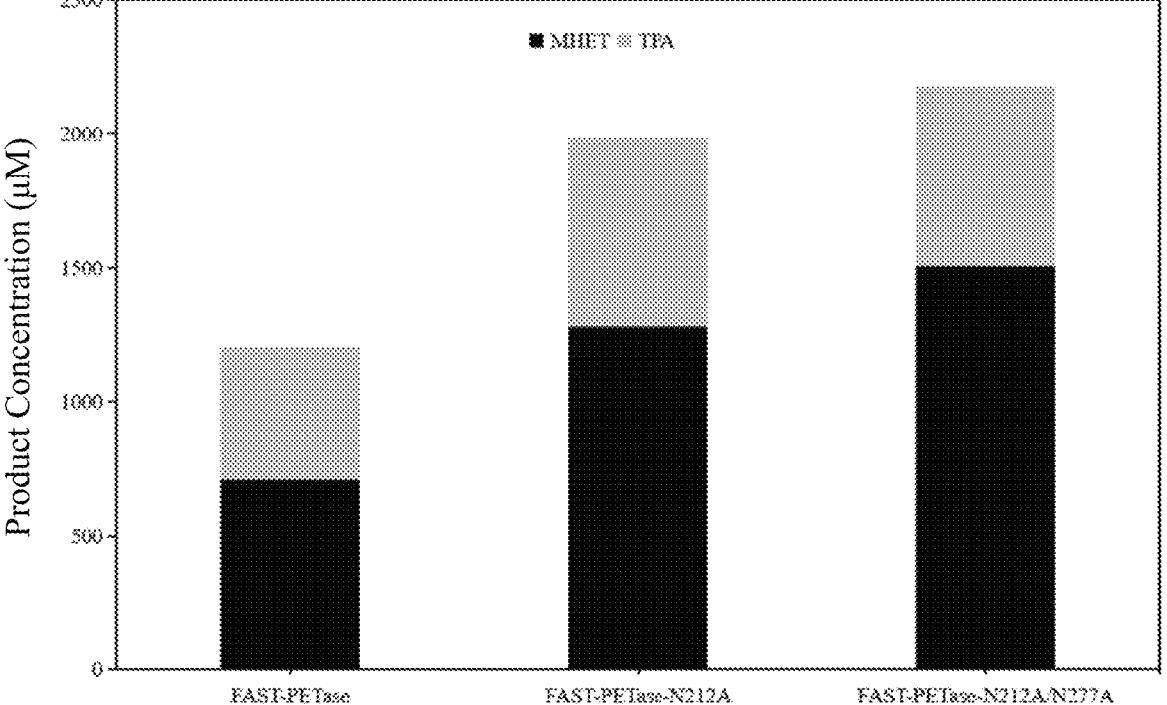
FIG. 8 shows the PET-hydrolytic activity analysis of FAST-PETase and the mutants.

FIG. 8 shows the PET-hydrolytic activity analysis of the FAST-PETase and the mutants. As shown in FIG. 8, under the reaction condition of 50° C., the PET-hydrolytic activities of the mutants FAST-PETase-N212A and FAST-PETase-N212A/N277A were both higher than that of the FAST-PETase. After reaction for 6 hours, the PET-hydrolytic activity of the FAST-PETase-N212A was 165% of that of the FAST-PETase, while the PET-hydrolytic activity of the FAST-PETase-N212A/N277A was 181% of that of the FAST-PETase. Therefore, the present invention significantly increased the PET-hydrolytic activities of the FAST-PETase-N212A and the FAST-PETase-N212A/N277A expressed in *P. pastoris*, which improves their application values in the PET degradation industry. Further, *P. pastoris* is capable of large-scale fermentation, and thus is suitable for high-density cultivation and beneficial for industrial scale-up production of recombinant proteins. Accordingly, the present invention successfully designed the high-yield and high-activity PET hydrolases.

In conclusion, in order to modify the FAST-PETase into a PET hydrolase having improved PET-hydrolytic activity, the present invention utilized structural analysis and site-directed mutagenesis to modify the FAST-PETase. The modified mutants FAST-PETase-N212A and FAST-PETase-N212A/N277A can be expressed in *P. pastoris*, and the PET-hydrolytic activities thereof are successfully improved, thereby obtaining high-yield and high-activity PET hydrolases, and enhancing the industrial application values of the PET hydrolases. Besides, the enzymes usually have some variations among different species but still have the same function, and most of them have at least 80%, 85%, 90% or 95% identity in amino acid sequence. Obviously, the enzymes are allowed to have some amino acid sequence variations but still maintain the enzyme function. In other words, the sequence of the modified PET hydrolase provided in the present invention is not limited to SEQ ID NO: 6 or 8, but also includes the sequence with at least 80%, 85%, 90% or 95% sequence identity of SEQ ID NO: 6 or 8 having the substitution of asparagine(s) at corresponding position(s) with alanine(s).

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A polyethylene terephthalate (PET) hydrolase having the full length amino acid sequence of SEQ ID NO: 6 or SEQ ID NO: 8.

* * * * *

SEQUENCE LISTING

```
Sequence total quantity: 8
SEQ ID NO: 1            moltype = DNA  length = 870
FEATURE                 Location/Qualifiers
source                  1..870
                        mol_type = other DNA
                        organism = synthetic construct
SEQUENCE: 1
atgaactttc cccgcgcttc ccgcctgatg caggccgccg ttctcggcgg gctgatggcc   60
gtgtcggccg ccgccaccgc ccagaccaac ccatacgcta gaggtccaaa cccaactgct  120
gcttctttgg aagcttctgc tggtccattc actgttaggt cttttactgt ttctagacca  180
tccggttacg gtgctggtac tgtttactac ccaactaacg ctggtggtac tgttggtgct  240
attgctattg ttcctggtta cactgctaga caatcttcta ttaagtggtg gggtccaaga  300
ttggcttctc atggtttcgt tgttattact attgacacta actctacttt agatcaacct  360
gaatctcgtt cttctcaaca aatggctgct ttgagacaag ttgcttcttt gaacggtact  420
tcttcttctc caatctacgg taaagttgat accgctagaa tgggtgttat gggttggtct  480
atgggtggtg gtggttcttt gatttctgct gctaataacc catccttgaa ggctgctgct  540
cctcaagctc cttggcattc ttctactaac tttctcttctg ttactgttcc aaccttgatt  600
tttgcatgtg aaaacgattc tatcgctcca gttaactctt ccgctttgcc aatctatgat  660
tctatgtctc aaaacgctaa gcaattttg gaaattaagg gtggttctca ttcttgtgct  720
aactctggta actctaacca agctttgatt ggtaaaaagg gtgttgcttg gatgaagcgt  780
tttatggata acgatactag atactctact tttgcttgtg aaaacccaaa ctctactgct  840
gtttctgact ttagaactgc taactgttct                                   870

SEQ ID NO: 2            moltype = AA  length = 290
FEATURE                 Location/Qualifiers
source                  1..290
                        mol_type = protein
                        organism = synthetic construct
SEQUENCE: 2
MNFPRASRLM QAAVLGGLMA VSAAATAQTN PYARGPNPTA ASLEASAGPF TVRSFTVSRP   60
SGYGAGTVYY PTNAGGTVGA IAIVPGYTAR QSSIKWWGPR LASHGFVVIT IDTNSTLDQP  120
ESRSSQQMAA LRQVASLNGT SSSPIYGKVD TARMGVMGWS MGGGGSLISA ANNPSLKAAA  180
PQAPWHSSTN FSSVTVPTLI FACENDSIAP VNSSALPIYD SMSQNAKQFL EIKGGSHSCA  240
NSGNSNQALI GKKGVAWMKR FMDNDTRYST FACENPNSTA VSDFRTANCS             290

SEQ ID NO: 3            moltype = DNA  length = 29
FEATURE                 Location/Qualifiers
```

-continued

```
source                    1..29
                          mol_type = other DNA
                          organism = synthetic construct
SEQUENCE: 3
ctccagttgc ttcttccgct ttgccaatc                                            29

SEQ ID NO: 4              moltype = DNA   length = 26
FEATURE                   Location/Qualifiers
source                    1..26
                          mol_type = other DNA
                          organism = synthetic construct
SEQUENCE: 4
cccagcttct actgctgttt ctgact                                               26

SEQ ID NO: 5              moltype = DNA   length = 870
FEATURE                   Location/Qualifiers
source                    1..870
                          mol_type = other DNA
                          organism = synthetic construct
SEQUENCE: 5
atgaactttc cccgcgcttc ccgcctgatg caggccgccg ttctcggcgg gctgatggcc         60
gtgtcggccg ccgccaccgc ccagaccaac ccatacgcta gaggtccaaa cccaactgct        120
gcttctttgg aagcttctgc tggtccattc actgttaggt cttttactgt ttctagacca        180
tccggttacg gtgctggtac tgtttactac ccaactaacg ctggtggtac tgttggtgct        240
attgctattg ttcctggtta cactgctaga caatcttcta ttaagtggtg gggtccaaga        300
ttggcttctc atggtttcgt tgttattact attgacacta actctacttt agatcaacct        360
gaatctcgtt cttctcaaca aatggctgct ttgagacaag ttgcttcttt gaacggtact        420
tcttcttctc caatctacgg taaagttgat accgctagaa tgggtgttat gggttggtct        480
atgggtggtg gtgttctttt gatttctgct gctaataacc catccttgaa ggctgctgct        540
cctcaagctc cttggcattc ttctactaac ttttcttctg ttactgttcc aaccttgatt        600
tttgcatgtg aaaacgattc tatcgctcca gttgcttctt ccgctttgcc aatctatgat        660
tctatgtctc aaaacgctaa gcaatttttg gaaattaagg gtggttctca ttcttgtgct        720
aactctggta actctaacca agctttgatt ggtaaaaagg gtgttgcttg gatgaagcgt        780
tttatggata acgatactag atactctact tttgcttgtg aaaacccaaa ctctactgct        840
gtttctgact ttagaactgc taactgttct                                         870

SEQ ID NO: 6              moltype = AA   length = 290
FEATURE                   Location/Qualifiers
source                    1..290
                          mol_type = protein
                          organism = synthetic construct
SEQUENCE: 6
MNFPRASRLM QAAVLGGLMA VSAAATAQTN PYARGPNPTA ASLEASAGPF TVRSFTVSRP          60
SGYGAGTVYY PTNAGGTVGA IAIVPGYTAR QSSIKWWGPR LASHGFVVIT IDTNSTLDQP        120
ESRSSQQMAA LRQVASLNGT SSSPIYGKVD TARMGVMGWS MGGGGSLISA ANNPSLKAAA        180
PQAPWHSSTN FSSVTVPTLI FACENDSIAP VASSALPIYD SMSQNAKQFL EIKGGSHSCA        240
NSGNSNQALI GKKGVAWMKR FMDNDTRYST FACENPNSTA VSDFRTANCS                   290

SEQ ID NO: 7              moltype = DNA   length = 870
FEATURE                   Location/Qualifiers
source                    1..870
                          mol_type = other DNA
                          organism = synthetic construct
SEQUENCE: 7
atgaactttc cccgcgcttc ccgcctgatg caggccgccg ttctcggcgg gctgatggcc         60
gtgtcggccg ccgccaccgc ccagaccaac ccatacgcta gaggtccaaa cccaactgct        120
gcttctttgg aagcttctgc tggtccattc actgttaggt cttttactgt ttctagacca        180
tccggttacg gtgctggtac tgtttactac ccaactaacg ctggtggtac tgttggtgct        240
attgctattg ttcctggtta cactgctaga caatcttcta ttaagtggtg gggtccaaga        300
ttggcttctc atggtttcgt tgttattact attgacacta actctacttt agatcaacct        360
gaatctcgtt cttctcaaca aatggctgct ttgagacaag ttgcttcttt gaacggtact        420
tcttcttctc caatctacgg taaagttgat accgctagaa tgggtgttat gggttggtct        480
atgggtggtg gtgttctttt gatttctgct gctaataacc catccttgaa ggctgctgct        540
cctcaagctc cttggcattc ttctactaac ttttcttctg ttactgttcc aaccttgatt        600
tttgcatgtg aaaacgattc tatcgctcca gttgcttctt ccgctttgcc aatctatgat        660
tctatgtctc aaaacgctaa gcaatttttg gaaattaagg gtggttctca ttcttgtgct        720
aactctggta actctaacca agctttgatt ggtaaaaagg gtgttgcttg gatgaagcgt        780
tttatggata acgatactag atactctact tttgcttgtg aaaacccagc ttctactgct        840
gtttctgact ttagaactgc taactgttct                                         870

SEQ ID NO: 8              moltype = AA   length = 290
FEATURE                   Location/Qualifiers
source                    1..290
                          mol_type = protein
                          organism = synthetic construct
SEQUENCE: 8
MNFPRASRLM QAAVLGGLMA VSAAATAQTN PYARGPNPTA ASLEASAGPF TVRSFTVSRP          60
SGYGAGTVYY PTNAGGTVGA IAIVPGYTAR QSSIKWWGPR LASHGFVVIT IDTNSTLDQP        120
ESRSSQQMAA LRQVASLNGT SSSPIYGKVD TARMGVMGWS MGGGGSLISA ANNPSLKAAA        180
```

-continued

```
PQAPWHSSTN FSSVTVPTLI FACENDSIAP VASSALPIYD SMSQNAKQFL EIKGGSHSCA  240
NSGNSNQALI GKKGVAWMKR FMDNDTRYST FACENPASTA VSDFRTANCS             290
```